United States Patent [19]

Krebs et al.

[11] Patent Number: 5,304,650
[45] Date of Patent: Apr. 19, 1994

[54] PROCESS FOR THE PREPARATION OF ALKYL N-(HYDROXYALKYL)-CARBAMATES

[75] Inventors: Andreas Krebs, Odenthal-Holz; Bernd-Wieland Krüger, Bergisch Gladbach, both of Fed. Rep. of Germany

[73] Assignee: Bayer Aktiengesellschaft, Leverkusen, Fed. Rep. of Germany

[21] Appl. No.: 955,003

[22] Filed: Oct. 1, 1992

[30] Foreign Application Priority Data

Oct. 10, 1991 [DE] Fed. Rep. of Germany ....... 4133516

[51] Int. Cl.$^5$ ................... C07D 211/60; C07C 261/00
[52] U.S. Cl. ..................................... 546/245; 560/157; 560/160
[58] Field of Search ................. 546/245; 560/157, 160

[56] References Cited

U.S. PATENT DOCUMENTS

4,900,834 2/1990 Kruger et al. ...................... 546/245
5,008,261 4/1991 Kruger et al. ...................... 514/212

FOREIGN PATENT DOCUMENTS

0289842 4/1988 European Pat. Off. .
1150973 7/1960 Fed. Rep. of Germany .
3239390 10/1982 Fed. Rep. of Germany .

OTHER PUBLICATIONS

Chemical Abstracts, 1984, p. 618.
William Carruthers, 1988, J. Chem. Soc. Perkin Trans. I, pp. 2251-2253.
W. Gordon Rose, *Journal of the American Chemical Society*, 1947, pp. 1384-1387.
William Braker, J. Chem. Soc. Perkin Trans I, 1988, p. 1963.

*Primary Examiner*—C. Warren Ivy
*Assistant Examiner*—Raymond Covington
*Attorney, Agent, or Firm*—Sprung Horn Kramer & Woods

[57] ABSTRACT

Alkyl N-(hydroxyalkyl)-carbamates of the formula (I)

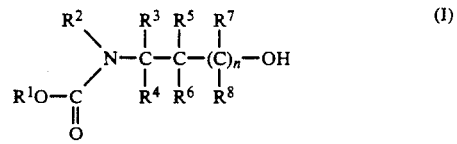

in which $R^1$ represents alkyl and $R^2$ to $R^8$ are identical or different and represent hydrogen or alkyl, or $R^2$ and $R^3$ together with the atoms to which they are bonded, form an optionally alkyl-substituted monocyclic ring, and n denotes 0 or 1, can be obtained in high purity and very good space-time-yields when amino alcohols of the formula (II)

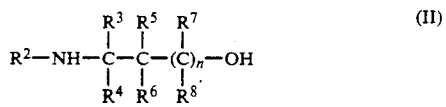

in which $R^2$ to $R^8$ and n have the abovementioned meaning are reacted with chloroformates of the formula (III)

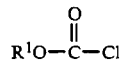

in which $R^1$ has the abovementioned meaning, in the presence of aqueous alkali metal hydroxide solutions and if appropriate in the presence of an organic solvent at temperatures between 30° C. and 110° C.

The substances prepared according to the invention can be employed as active compounds in agents for repelling insects and mites (cf. EP-A 289,842).

9 Claims, No Drawings

PROCESS FOR THE PREPARATION OF ALKYL N-(HYDROXYALKYL)-CARBAMATES

The present invention relates to a new process for the preparation of known alkyl N-(hydroxyalkyl)-carbamates.

It has already been disclosed that alkyl N-(hydroxyalkyl)-carbamates can be obtained by reacting amino alcohols with chloroformates. This reaction is customarily carried out in an inert organic solvent in the presence of an acid acceptor at temperatures from $-20°$ C. to $+20°$ C. Examples which may be mentioned are the reaction of 2-methylamino-ethanol with benzyl chloroformate and triethylamine in chloroform at 20° C. (DE-A 3,239,390), of 2-(2-hydroxyethyl)-piperidine with butyl chloroformate and triethylamine in tetrahydrofuran at $-20°$ C. (EP-A 289,842) and the reaction of 2,2-diethyl-3-hydroxypropylamine with ethyl chloroformate and triethylamine in benzene, with cooling, followed by refluxing for 2.5 hours (German Patent Specification 1,150,973). It is also known that 2-(2-hydroxyethyl)-piperidine can be reacted with methyl chloroformate at 0° to 20° C. in the presence of an aqueous sodium hydrogen carbonate solution to give methyl 2-(2-hydroxyethyl)-piperidinyl-carbamate (J. Chem. Soc. Perkin Trans. I 1988, 2251 to 2253). It is furthermore known that 2-aminoethanol can be reacted with benzyl chloroformate at 0° C. using 4N sodium hydroxide solution as acid acceptor to give benzyl N-(2-hydroxy-ethyl)-carbamate [J. Am. Chem. Soc. 69, 1384 (1947)].

The processes mentioned generally exhibit a series of disadvantages which make scaling-up to an industrial scale difficult or impossible: the raw materials are frequently contaminated and must be purified by distillation or by chromatography, which not only increases the complexity but can also lead to considerable yield losses. The consequence of the principal secondary reaction is the formation of products which are derived from a competing reaction of the chloroformate with the hydroxyl group. When the purification is carried out by distillation, decomposition reactions can occur even at low pressures whose malodorous products contaminate the distillate. Moreover, the use of tertiary amines as acid acceptors results in a more complex working-up or disposal of the resulting amine hydrochlorides. Under industrial conditions, reaction temperatures of 0° to 20° C. result in long reaction times so that the heat of the highly exothermic reaction can be dissipated.

There was therefore a demand for a process for reacting chloroformates with N-(hydroxyalkyl)-amines which is simple to carry out and gives sufficiently pure products in high yields and very good space-time-yields without problems during working-up.

It has now been found that alkyl N-(hydroxyalkyl) carbamates of the formula (I)

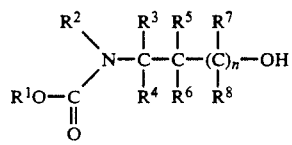

in which $R^1$ represents alkyl and $R^2$ to $R^8$ are identical or different and represent hydrogen or alkyl, or $R^2$ and $R^3$ together with the atoms to which they are bonded form an optionally alkyl-substituted monocyclic ring and n denotes 0 or 1, can be obtained when aminoalcohols of the formula (II)

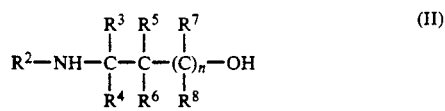

in which $R^2$ to $R^8$ and n have the abovementioned meaning are reacted with chloroformates of the formula (III)

in which $R^1$ has the abovementioned meaning in the presence of aqueous alkali metal hydroxide solutions and, if appropriate, in the presence of an organic solvent at temperatures between 30° C. and 110° C.

The process according to the invention has a series of advantages: for example, the yields are very high and are as much as 80 to over 90% of theory. The space-time-yields are also very good since the reaction can be carried out with little, or even without, solvent and with relatively concentrated acid acceptor solutions. Moreover, few secondary products are formed in the process, so that product purities of more than 98% can be achieved after simple working-up steps. Finally, the reaction temperatures of 30° to 110° C. permit the reactor to be water-cooled.

It must be regarded as extremely surprising that such good yields can be achieved by the process according to the invention, since it is generally known that chloroformates are rapidly hydrolysed by water and, in particular, by aqueous alkali metal hydroxide solutions. This applies in particular to higher reaction temperatures. Moreover, it was completely unexpected that purer reaction products are obtained when the reaction temperatures are higher rather than when they are lower (compare, for example: R. T. Morrison and R. N. Boyd, Lehrbuch der organischen Chemie [Textbook of Organic Chemistry], p. 128, 3rd Edition, Verlag Chemie, Weinheim, 1986: "Es ist eine allgemeine Tatsache, dass mit einer Erhöhung der Temperatur die Selektivite,uml/a/ t eines Reagenzes hinsichtlich der Angriffs-Position abnimmt, ungekehrt wächst die Selektivität mit sinkender Temperatur" [It is a general fact that the selectivity of a reagent with regard to the position of the attack decreases with increasing temperature, and, conversely, the selectivity increases with decreasing temperature.]

If, for example, 2-(2-hydroxyethyl)-piperidine and sec.-butyl chloroformate are used as starting materials, the course of the reaction can be represented by the following equation:

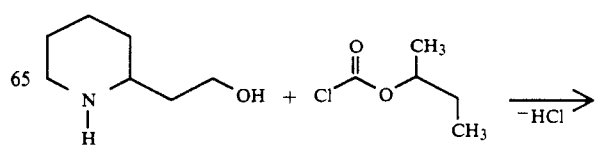

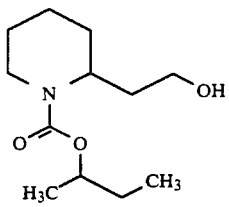

In formulae (I) and (II), the radicals $R^2$ to $R^8$ preferably represent hydrogen or alkyl radicals having 1 to 8 carbon atoms. Examples of the alkyl radicals which may be mentioned are methyl, ethyl, n- and i-propyl, n-, i- and t-butyl, n-pentyl, n-hexyl and 2-ethyl-hexyl. If $R^2$ and $R^3$ together with the atoms to which they are bonded form a ring, then preferred rings are those which have 5 to 7 atoms and which can be substituted by $C_1$–$C_4$-alkyl radicals. The letter n represents 0 or 1.

Particularly preferred compounds of the formulae (I) and (II) are those in which the radicals $R^2$ to $R^8$ represent hydrogen, methyl or ethyl, or the radicals $R^2$ and $R^3$ together with the atoms to which they are bonded form an unsubstituted ring which has 5 to 7 atoms and where n denotes 0 or 1.

Very particularly preferred are compounds of formulae (I) and (II) in which $R^2$ represents methyl and $R^3$ to $R^8$ represent hydrogen or in which the radicals $R^2$ and $R^3$ together with the atoms to which they are bonded represent the piperidine ring and n represents 1.

The compounds of the formula (II) are already known (compare, for example, Cesare Ferri, Reaktionen der org. Synthese [Reactions in Organic Synthesis], Georg Thieme Verlag Stuttgart, 1978, p. 211 et seq. and 496 to 497).

Examples of the starting substances of the formula (II) which may be mentioned are:
2-amino-ethanol
2-methylamino-ethanol
2-ethylamino-ethanol
3-amino-propanol
3-methylamino-propanol
1-amino-2-propanol
2-amino-1-butanol
2-amino-2-methyl-propanol
2-(2-hydroxyethyl)-piperidine
2-hydroxymethyl-piperidine
2-hydroxymethyl-pyrrolidine
2-hydroxy-ethyl)-pyrrolidine In formula (III), the radical $R^1$ preferably represents straight-chain or branched alkyl having 1 to 12 carbon atoms. Particularly preferred compounds of the formula (III) are those in which $R^1$ represents a straight-chain or branched alkyl radical having 1 to 5 carbon atoms.

Examples of the compounds of the formula (III) which may be mentioned are:
methyl chloroformate
ethyl chloroformate
1-methyl-ethyl chloroformate
propyl chloroformate
1-methyl-propyl chloroformate
2-methyl-propyl chloroformate
2,2-dimethyl-propyl chloroformate
butyl chloroformate
1-methyl-butyl chloroformate
2-methyl-butyl chloroformate
3-methyl-butyl chloroformate
1,3-dimethyl-butyl chloroformate
3,3-dimethyl-butyl chloroformate
2-ethyl-butyl chloroformate
pentyl chloroformate
2-methyl-pentyl chloroformate
hexyl chloroformate
2-ethyl-hexyl chloroformate For example, the alkyl N-(hydroxyalkyl)-carbamates of the formula (I) which can be prepared according to the invention are disclosed in EP-A 289,842.

Suitable diluents for the process according to the invention are all inert organic solvents These preferably include hydrocarbons such as petroleum ether, ligroin, hexane, cyclohexane, methylcyclohexane, toluene and xylene, ethers such as diethyl ether, diisopropyl ether, methyl tert.-butyl ether, methyl tert.-amyl ether and anisole as well as halogenated hydrocarbons such as dichloromethane, 1,1,2-trifluoro-trichloro-ethane, chlorobenzene and 1,2-dichlorobenzene, and their mixtures. However, the reaction can also be carried out without solvent or using the reaction product or a by-product from the chloroformate, the corresponding carbonate, as the diluent.

The reaction according to the invention is carried out in the presence of aqueous alkali metal hydroxide solutions as acid acceptors. Examples which may be mentioned are lithium hydroxide, sodium hydroxide and potassium hydroxide. Aqueous sodium hydroxide solution is preferably employed.

The reaction is carried out at temperatures between 30° and 110° C., preferably between 50° and 90° C.

The reaction can be carried out under atmospheric pressure, but also under increased or reduced pressure. In general, the process is carried out under atmospheric pressure.

When carrying out the process according to the invention, 0.6 to 1.3 mol of the reactant of the formula (III) are employed per mole of the starting material of the formula (II). It is preferred to react one mole of the starting material of the formula (II) with 0.8 to 1.0 mol of the reactant of the formula (III). The alkali metal hydroxide is employed in amounts of from 0.9 to 2.0 mol per mole of the reactant of the formula (III). It is preferred to use 1.0 to 1.2 mol of alkali metal hydroxide.

When carrying out the process according to the invention, the reaction may be conducted in several ways. For example, the starting material of the formula (II) is introduced together with the aqueous alkali metal hydroxide solution, and the reactant of the formula (III) is metered in. However, it is also possible to introduce the starting material of the formula (II), optionally in the form of an aqueous solution, and to meter in the reactant of the formula (III) and the alkali metal hydroxide solution simultaneously, or to introduce the alkali metal hydroxide solution and to meter in the two reactants simultaneously. Moreover, it is possible to meter the two reactants and the alkali metal hydroxide solution simultaneously into a reactor.

Suitable reaction containers are the customary reactors, for example reaction vessels, cascades of reaction vessels and tubular reactors The reaction temperature of the process according to the invention can be reached by several ways, for example by preheating the reactant of the formula (II) and the alkali metal hydroxide solution and/or by utilising the heat of the reaction.

Working-up is carried out by customary methods, for example by separating off the aqueous phase and washing the organic phase with dilute mineral acids and with water, it being possible to dilute the organic phase, if appropriate, with a solvent which is not miscible with water. Contaminants which are more readily volatile can be removed by so-called "incipient distillation", that is to say by prolonged heating to a moderately increased temperature under reduced pressure, it being possible, if appropriate, to add water or to blow in steam, so as to facilitate the removal of steam-volatile contaminants.

The substances prepared according to the invention can be employed as agents for repelling insects and mites (cf. EP-A 289,842).

PREPARATION EXAMPLE

Example 1

Sec.-butyl 2-(2-hydroxyethyl)-piperidyl-carbamate

In a 1.0 l reaction container equipped at the bottom with an outlet valve there are dissolved 258.4 g (2 mol) of 2-(2-hydroxyethyl)-piperidine in 249 g of water at 60° C., 195.5 g (2.2 mol) of 45 % strength sodium hydroxide solution are added, and 259.4 g (1.9 mol) of 1-methylpropyl chloroformate are added dropwise at an internal temperature of 60° C. and with vigorous stirring in such a way that the internal temperature reaches 80° C. (duration 40 minutes). The internal temperature is then lowered to 25° C., the aqueous phase is removed, and the organic phase is treated with 340 ml of methylcyclohexane. This is extracted by stirring twice using 120 ml of 1N sulphuric acid in each case, where each extraction is carried out over 5 minutes, the batch is then washed four times until neutral, using 120 ml of water in each case, and the methylcyclohexane is removed by distillation at 18 mbar into a receiving vessel which is subjected to intense cooling, until the internal temperature had reached 80° C. The product is allowed to cool to 30° C. in vacuo, 20 ml of water are added, and the mixture is stirred until homogeneous and subjected to distillation at 30° C./18 mbar. This procedure is repeated, incipient distillation being carried out up to an internal temperature of 60° C.

Yield: 408.1 g
Purity: 99.2%
(=92.9% of theory based on the chloroformate)

Example 2

Sec.-butyl 2-(2-hydroxyethyl)-piperidinyl-carbamate

Into a 20 l reaction container equipped with an outlet valve at the bottom there are introduced 2,192 g (24.66 mol) of 45% strength sodium hydroxide solution, and 2,896 g of 2-(2-hydroxyethyl)-piperidine (purity after titration with perchloric acid 98.2%, = 22 mol) in the form of a solution in 2,800 g of water.

Starting at an internal temperature of 50° C. and a jacket temperature of 50° C., 2,907 g of sec.-butyl chloroformate (97.5% pure, = 20.75 mol) are then metered in with stirring in the course of 60 minutes, during which process the internal temperature rises to 80° C. after approx. 1,000 g and 20 minutes, whereupon the jacket temperature is lowered to 30° C. to maintain an internal temperature of 80° to 85° C. The mixture is then cooled to 20° C. in the course of 1 hour, with stirring, and the aqueous phase is separated off. 3.8 l of n-hexane are added to the organic phase, and the batch is extracted three times by stirring with 1,345 ml of 1N sulphuric acid in each case. The mixture is then extracted by stirring with 1,345 ml of water in each case until the aqueous phase has a pH of 5 to 6. At a jacket temperature of 25° C. and a slowly increasing vacuum, the n-hexane and the residual moisture are then removed by distillation into a receiving vessel which is subjected to intensive cooling. Once 30 mbar have been reached, the internal temperature is increased to 80° C. The mixture is subsequently subjected to incipient distillation at 0.1 mbar/80° C. for 15 minutes and cooled to 20° C. in vacuo.

Yield: 4,530 g
GC purity: 99.3%
= 89.1% based on 2-(2-hydroxyethyl)-piperidine
= 94.5% based on sec.-butyl chloroformate

Examples 3 to 20

0.1 mol of amino alcohol are dissolved or suspended in 100 ml of diluent, and 9.8 g (0.11 mol) of 45% strength sodium hydroxide solution and 12.9 ml of water are added, and the mixture is stirred until all components have dissolved. 0.09 mol of chloroformate are then added dropwise with vigorous stirring in the course of 10 minutes at 20° C. (comparison) with cooling, or, according to the invention, at boiling point or 80° C. Stirring is continued for 30 minutes, and, if appropriate, the mixture is cooled to room temperature. The aqueous phase is then separated off, the organic phase is washed with 1N sulphuric acid and with water, and the solvent is removed on a rotary evaporator. The residue is subjected to incipient distillation at up to 50° C./0.1 mbar.

A measure of the purity of the reaction product is the diacylated product content [see, in this context, the table below: compound of the formula (IV)]. The table shows that the selectivity of the reaction is markedly better in the process according to the invention than when carried out at lower temperatures.

TABLE

| Ex. No. | Compound II | Compound III (ClCO$_2$R$^1$) R$^2$ = | Solvent | Temp. [°C.] | Yield I [%, based on III] | By-product content IV* [%] |
|---|---|---|---|---|---|---|
| 3 | piperidine-CH$_2$CH$_2$OH (N-H) | CH$_3$ | toluene | 20 | 94 | 4.5 |
| 4 | " | " | " | 80 | 93 | 1.5 |
| 5 | " | C$_2$H$_5$ | " | 20 | 91 | 2.7 |
| 6 | " | " | " | 80 | 93 | 1.4 |

TABLE-continued

| Ex. No. | Compound II | Compound III (ClCO$_2$R$^1$) R$^2$ = | Solvent | Temp. [°C.] | Yield I [%, based on III] | By-product content IV* [%] |
|---|---|---|---|---|---|---|
| 7 | " | —CH(CH$_3$)—C$_2$H$_5$ | " | 20 | 85 | 2.7 |
| 8 | " | " | " | 80 | 88 | 0.7 |
| 9 | " | " | cyclohexane | 20 | 78 | 4.5 |
| 10 | " | " | cyclohexane | 80 | 90 | 0.9 |
| 11 | " | " | methyl tert.-butyl ether | 20 | 91 | 1.8 |
| 12 | 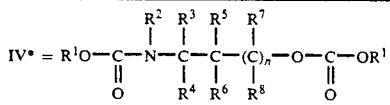 | —CH(CH$_3$)—C$_2$H$_5$ | methyl tert.-butyl ether | 55 | 88 | 0.7 |
| 13 | " | —CH$_2$—CH(C$_2$H$_5$)—C$_4$H$_9$ | toluene | 20 | 86 | 2.9 |
| 14 | " | " | " | 80 | 86 | 1.7 |
| 15 | H$_2$N—CH$_2$—CH$_2$—OH | CH(CH$_3$)—C$_2$H$_5$ | " | 20 | 87 | 5.7 |
| 16 | " | " | " | 80 | 83 | <0.1 |
| 17 | H$_2$N—C(CH$_3$)$_2$—CH$_2$—OH | " | " | 20 | 86 | 2.4 |
| 18 | " | " | " | 80 | 90 | 0.3 |
| 19 | H$_3$C—NH—CH$_2$—CH$_2$—CH$_2$—OH | —CH$_2$—CH$_2$—CH(CH$_3$)$_2$ | toluene | 20 | 84 | 1.3 |
| 20 | H$_3$C—NH—CH$_2$—CH$_2$—CH$_2$—OH | —CH$_2$—CH$_2$—CH(CH$_3$)$_2$ | " | 80 | 90 | <0.1 |

$$IV^* = R^1O-\underset{O}{\underset{\|}{C}}-\underset{R^4}{\underset{|}{N}}-\underset{R^6}{\underset{|}{\overset{R^3}{\underset{|}{C}}}}-\underset{R^8}{\underset{|}{\overset{R^5}{\underset{|}{C}}}}-(C)_n-O-\underset{O}{\underset{\|}{C}}-OR^1$$
with R$^2$, R$^7$ on top carbons.

Example 21

The procedure is as in Example 1, except that 2-(2-hydroxyethyl)-piperidine is introduced as the aqueous solution and the 45% strength sodium hydroxide solution and sec.-butyl chloroformate are metered in simultaneously in such a way that a pH of 10.5 to 11.5 is maintained. 414.1 g of sec.-butyl 2-(2-hydroxyethyl)-piperidinyl-carbamate with a purity of 99.0% as determined by gas chromatography, which corresponds to a yield of 94.1% of theory.

Comparison Example A

Analogously to EP-A 289,842, 6.5 g (0.05 mol) of 2-(2-hydroxyethyl)-piperidine and 10 ml of triethylamine are dissolved in 300 ml of analytical-grade tetrahydrofuran, and the mixture is treated at −20° C. with 6.48 g (47.5 mmol) of sec.-butyl chloroformate. Stirring is then continued for 24 hours at 20° C., and the mixture is extracted with dichloromethane/water. The organic phase is dried using magnesium sulphate, and the solvent is then removed in vacuo on a rotary evaporator, and the residue is subjected to incipient distillation up to 50° C./0.1 mbar. 10.2 g of a crude product are obtained, which contains, according to analysis by gas chromatography, 73% of sec.-butyl 2-(2-hydroxyethyl)-piperidinyl-carbamate and 24% of sec.-butyl 2-[2-(sec.-butyloxy-carbonyl)-ethyl]-piperidinyl-carbamate.

Comparison Example B

Analogously to J. Am. Chem. Soc. 69, 1384 (1947), 12.9 g (0.1 mol) of 2-(2-hydroxyethyl)-piperidine are dissolved in 12.5 ml of water, this mixture is introduced into the reaction vessel, and 25 ml of 4N sodium hydroxide solution and 12.9 g (0.095 mol) of sec.-butyl-chloroformate are simultaneously added dropwise at 0° to 3° C., with ice-cooling. Stirring is continued for 30 minutes at 0° C. and for 30 minutes at room temperature. The batch is extracted with ether, the extract is washed twice using 1N hydrochloric acid and then with water, dried over sodium sulphate and concentrated on a rotary evaporator, and the residue is subjected to incipient distillation at 50° C./0.1 mbar. 18.3 g of a crude product are obtained which contains, according to analysis by gas chromatography, 91.8% of sec.-butyl 2-(2-hydroxyethyl)-piperidinyl-carbamate and 7.6% of sec.-butyl 2-[2-(sec.-butyloxy-carbonyl)-ethyl]-piperidinyl-carbamate. This means that in this case too the diacylated product content is substantially greater than in the process according to the invention.

We claim:

1. Process for the preparation in relatively high yield and purity of alkyl N-(hydroxy-alkyl)-carbamates of the formula (I)

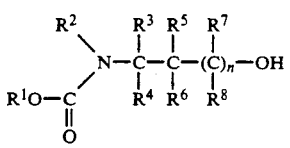

in which $R^1$ represents alkyl the radicals $R^2$ to $R^8$ represent hydrogen, methyl or ethyl or the radicals $R^2$ and $R^3$ together with the atoms to which they are bonded stand an unsubstituted ring having 5 to 7 atoms, and n denotes 0 or 1 n denotes 0 or 1, by reacting amino alcohols of the formula (II)

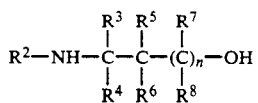

in which $R^2$ to $R^6$ and n have the abovementioned meaning, with chloroformates of the formula (III)

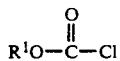

in which $R^1$ has the abovementioned meaning, characterised in that the reaction is carried out in the presence of aqueous alkali metal hydroxide solutions and, if appropriate, in the presence of an organic solvent at temperatures between 30 and 110° C.

2. Process according to claim 1, characterised in that the process is carried out in the temperature range between 50° and 90° C.

3. Process according to claim 1 characterised in that aqueous solutions of sodium hydroxide are employed as alkali metal hydroxide solutions.

4. Process according to claim 1 characterised in that 0.6 to 1.3 mol of chloroformate of the formula (III) are employed per mole of amino alcohol of the formula (II).

5. Process according to claim 1 characterised in that 0.8 to 1.0 mol of chloroformate of the formula (III) are employed per mole of amino alcohol of the formula (II).

6. Process according to claim 1 characterised in that 0.9 to 2.0 mol of alkali metal hydroxide are employed per mole of chloroformate of the formula (III).

7. Process according to claim 1 characterised in that 1.0 to 1.2 moles of alkali metal hydroxide are employed per mole of chloroformate of the formula (III).

8. Process according to claim 1 for the preparation of compounds of the general formula (I) in which the radicals $R^2$ to $R^8$ represent hydrogen or alkyl ($C_1$-$C_8$), or $R^2$ and $R^3$ together with the atoms to which they are bonded represent a ring which has 5 to 7 atoms and which is optionally substituted by alkyl-($C_1$-$C_4$), and n represents 0 or 1.

9. Process according to claim 1 for the preparation of compounds of the general formula (I) in which $R^2$ represents methyl, $R^3$ to $R^8$ represent hydrogen, or where $R^2$ and $R^3$ together with the atoms to which they are bonded denote the piperidine ring, and n represents 1.

* * * * *